US008597234B2

(12) United States Patent
Larsson

(10) Patent No.: US 8,597,234 B2
(45) Date of Patent: Dec. 3, 2013

(54) BREAST SHIELD WITH SENSOR

(75) Inventor: Michael Larsson, Zug (CH)

(73) Assignee: Medela AG (CH)

( * ) Notice: Subject to any disclaimer, the term of this patent is extended or adjusted under 35 U.S.C. 154(b) by 3469 days.

(21) Appl. No.: 10/918,280

(22) Filed: Aug. 13, 2004

(65) Prior Publication Data

US 2005/0059928 A1    Mar. 17, 2005

Related U.S. Application Data

(63) Continuation-in-part of application No. 10/503,673, filed as application No. PCT/CH03/00094 on Feb. 7, 2003, now abandoned, which is a continuation-in-part of application No. PCT/CH02/00073, filed on Feb. 7, 2002.

(30) Foreign Application Priority Data

Feb. 7, 2002   (WO) .................. PCT/CH02/00073
Feb. 7, 2003   (WO) .................. PCT/CH03/00094

(51) Int. Cl.
 *A61M 1/06*  (2006.01)
(52) U.S. Cl.
 USPC .............................................. 604/74
(58) Field of Classification Search
 USPC .............................................. 604/74
 See application file for complete search history.

(56) References Cited

U.S. PATENT DOCUMENTS 5,827,191 A * 10/1998 Rosenfeld ............... 600/476
5,830,159 A    11/1998 Netta
6,179,783 B1    1/2001 Mohler
6,314,315 B1 * 11/2001 Hung et al. ............... 600/547

FOREIGN PATENT DOCUMENTS

| DE | 3429057 A | 2/1986 |
|----|-----------|--------|
| EP | 0 875 257 A1 | 4/1997 |
| EP | 875257 A | 11/1998 |
| WO | 96/12439 | 5/1996 |
| WO | WO 00/41618 | 7/2000 |
| WO | WO 00/47247 | 8/2000 |
| WO | WO 01/54488 A1 | 8/2001 |

* cited by examiner

*Primary Examiner* — Jason Flick
(74) *Attorney, Agent, or Firm* — McDonnell Boehnen Hulbert & Berghoff LLP

(57) ABSTRACT

A presently preferred embodiment of the invention includes a breast shield for use on a human breast including a breast-receiving portion, which is sized and shaped to receive a nipple and at least some surrounding breast. One or more sensors are connected to the breast-receiving portion and capable of sensing changes in the breast. Alternate embodiments of this aspect of the present invention include a sensor being one or more, for example, of an optical sensor, an electrode, a thermal sensor and an acoustic sensor. The optical sensor may be adapted to detect changes in light reflected from the breast. The electrode may be a pair of electrode parts, a first of which is used to apply an output voltage to the breast and a second of which is used to receive current conducted from the first of the pair of electrode parts. The acoustic sensor may be adapted to detect changes in breast tissue.

7 Claims, 4 Drawing Sheets

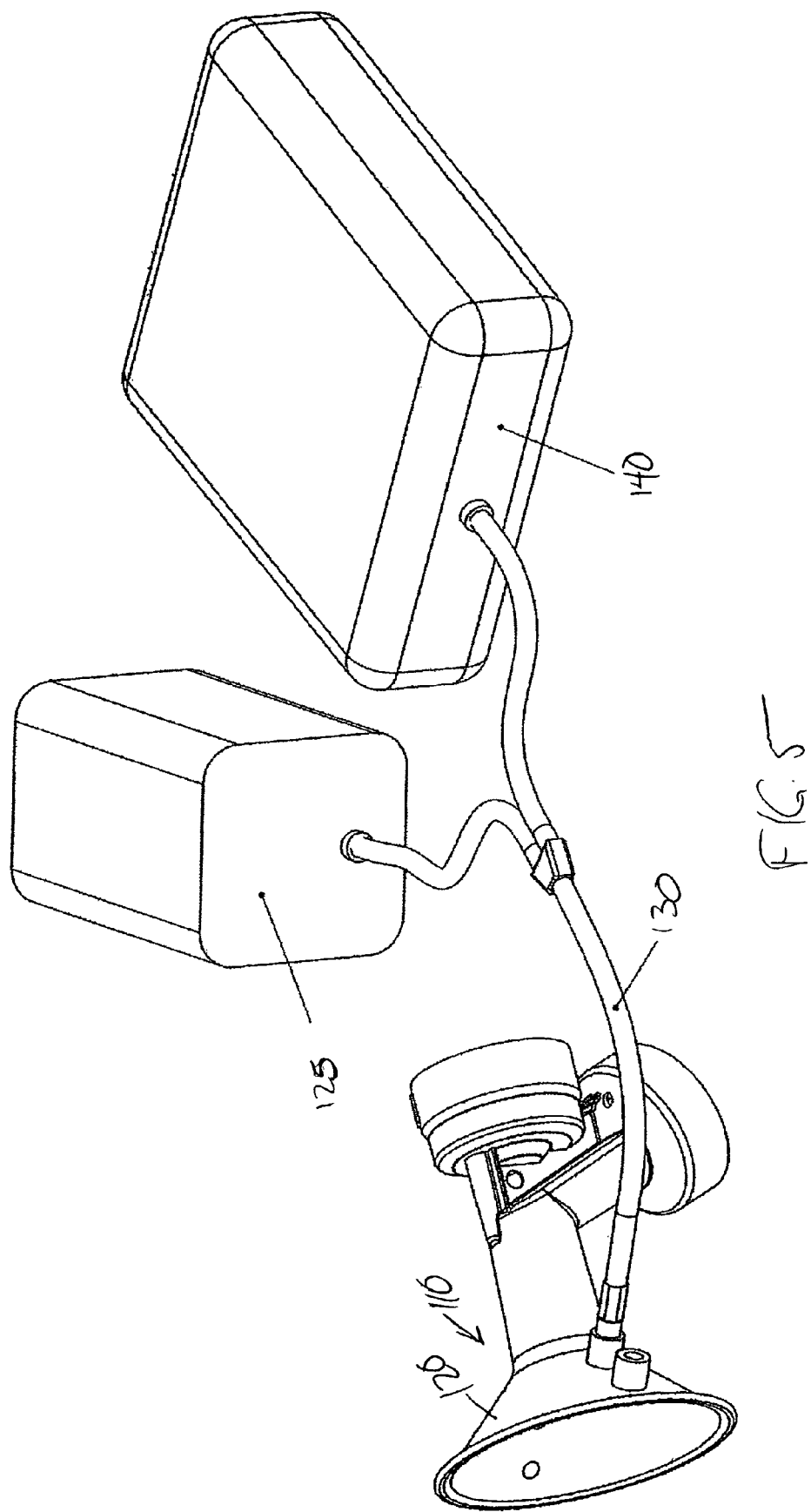

BREAST SHIELD WITH SENSOR

PRIORITY CLAIM

This application is a continuation-in-part application of U.S. Ser. No. 10/503,673, filed Aug. 4, 2004 now abandoned, which was the National Stage Application of International Application No. PCT/CH03/00094, filed Feb. 7, 2003, which in turn claims priority to International Application No. PCT/CH02/00073, filed Feb. 7, 2002.

FIELD OF THE INVENTION

The present invention relates to a breast cup, commonly referred to as a breast shield, and to a device and method for detecting changes in a mother's breast during the process of expressing milk from the mother's breast.

BACKGROUND OF THE INVENTION

Breast cups or breast shields for breast pumps and similar suction devices for expressing breast milk are widely available in many different designs and are used all over the world. An example of such a breast shield and breast pump and the operation thereof is shown in U.S. Pat. No. 6,547,756.

Breast-feeding of a baby is not always straightforward. The causes of problems may lie with the mother or with the baby. Expressing breast milk by means of suction pumps or suction devices, also called breast pumps, can also be problematic for some mothers. Nowadays, therefore, in the development of suction pumps and of their operating conditions, increased efforts are being made to better understand what is going on inside the mother's breast during expression of breast milk. During use of a breastpump, however, it is difficult to carry out exact measurements on the mother's breast. Such measurements would, however, provide information on the processes going on during expression of breast milk during, for example, the stimulation phase and during the actual expression of milk. Furthermore, if available, it is contemplated that this information could be used in a number of useful ways.

There is a demand for a device, system and method that provides information during use of a breastpump. The present invention satisfies the demand.

SUMMARY OF THE INVENTION

It is therefore, an object of the present invention to make available a device and a method which permit straightforward measurement of the processes going on inside the breast, even during expression of milk. Another object of the present invention is to accurately and directly measure these processes.

The solution according to the present invention involves the use of a breast shield designed to accommodate and/or incorporate one or more types and/or variety of sensors. The sensors used can be any type of sensor suitable for detecting changes in the mother's breast, in particular, for example, electrodes, optical sensors, acoustic sensors and thermal sensors. It will be understood that the sensors contemplated are readily available and are in use in the medical field for monitoring and studying various biological phenomenon. For example, electrodes are currently used to study brain activity, muscle activity and other electrical biological functions. Acoustic sensors are currently used to study tissues with varying acoustic densities, in for example, prenatal imaging, and cancer detection and so on. Optical sensors are currently used to detect and monitor oxygen levels in skin tissues. Thermal sensors are currently used to measure temperature changes.

The field of sensors, and in particular, of biomedical sensors is a well studied and documented science. One may glean an extensive amount of information regarding specific construction, circuits, analysis of data and applications for these sensors, for example, by consulting such texts as: *Medical instrumentation: Application and design, 3rd ed.*, Webster J. G. (ed.), Wiley, 1998, (systems, sensors, circuits, hospital instrumentation, therapeutic devices, and safety); *Biomedical transducers and instruments*, Togawa T., Tamura T., Oberg P. A., CRC Press, 1997, (short descriptions of very many biomedical transducers); *Biomedical instruments: Theory and design, 2nd ed.*, Welkowitz W., Deutsch S., Akay M., Academic Press, 1992, (physical sensors, analog and digital circuits, 12 biomedical instrumentation designs, and medical imaging); *Principles of biomedical instrumentation and measurement*, Aston R., Merrill Publishing Co., 1990, (descriptive); *Principles of applied biomedical instrumentation, 3rd ed.*, Geddes L. A., Baker L. E., Wiley, 1989, (many sensors for biomedicine, and therapeutic devices); *Principles of bioinstrumentation*, Normann R. A., Wiley, 1988, (circuits, sensors for biomedicine, computers, signal processing, and safety); *Biomedical engineering and instrumentation*, Bronzino J. D., PWS Engineering, 1986, (many sensors for biomedicine, therapeutic devices, but omits the new fields); *Biomedical instrumentation and measurements, 2nd ed.*, Cromwell L., Weibell F. J., Pfeiffer E. A., Prentice-Hall, 1980, (descriptive); *Transducers for biomedical measurements*, Cobbold, R. S. C., Wiley, 1974, (systems, and many sensors for biomedicine).

Accordingly, various measurement methods are possible, for example, ultrasound, detection and measurement of electrical activity which records, for example, resistance and impedance between two spaced areas of the breast, and so on. Electrodes are placed on the breast skin for measuring electric signals, optical sensors for detecting and/or measuring, for example, light absorption or reflection, and acoustic sensors for detecting and/or measuring ultrasound. It will be understood that the sensors contemplated by the present invention can be conventional sensors, and the like, designed for detecting various changes in humans and, in particular, human breast tissue, including the skin. Other sensors may also be employed to study other phenomenon associated with breast pumping.

The design of the breast shield according to the invention allows measurements to be carried out on the breast in general and also during the expression of breast milk. The method according to the invention and the device according to the invention provide information in particular on the process known as milk surge and other phases of milk production.

The device and method of the present invention contemplates providing data regarding breast pumping for research purposes, for example, to further the understanding of the process of milk letdown and expression, as well as providing a signal or data in a control function, e.g., to a breastpump capable of analyzing the data and making adaptations in operation in reaction to the data/signal.

According to the present invention there are opportunities to add functionality to and even simplify the operation of a breast pump. One breast pump device that is particularly well suited to adaptability with respect to different operating parameters and phases is shown in U.S. Pat. No. 6,547,756, for example. This breast pump includes a programmable feature that would permit the device to operate according to a virtually unlimited set of parameters. In one embodiment of the invention, differing programs, data and other signal inputs may be provided to the pump at any time and even during functioning to change aspects of the operation of the pump. For example, the pump may change to or initiate different phases of operation in response to detected changes in the breast sensed by the device of the present invention. Manual breast pumps may, of course, be used in operation of certain aspects of the present invention.

An aspect of the present invention includes a breast shield for use on a human breast including a breast-receiving portion, sized and shaped to receive a nipple and at least some surrounding breast. One or more sensors are connected to the breast-receiving portion and capable of sensing changes in the human breast. Alternate embodiments of this aspect of the present invention include a sensor being one or more of an optical sensor, an electrode, a thermal sensor and an acoustic sensor. The optical sensor may be adapted to detect changes in light through or from the breast. The electrode may be a pair of electrode parts, a first of which is used to apply voltage to the breast and a second of which is used to receive current conducted from the first of the pair of electrode parts. The acoustic sensor may be adapted to detect changes in breast tissue, such as density or shape.

Another aspect of the present invention includes a method of sensing changes in a human breast including providing a breast shield with one or more sensors capable of sensing changes in the human breast, contacting a human breast with the breast shield and one or more sensors, applying a cyclical pressure (positive and/or negative) to the breast, and sensing changes in the breast by way of the one or more sensors. Alternate embodiments of this aspect of the present invention include measuring changes according to variations in conductance. The sensing of changes may include the sensing of thermal changes. The sensing of changes may include the sensing of changes in acoustic properties. The sensing of changes may include the sensing of changes in optical properties. Again, the sensors are not limited to just the foregoing, but will include any known to those skilled in the art, unless otherwise stated.

Yet another aspect of the present invention includes a method of controlling a microprocessor controlled breastpump including providing a breast shield with one or more sensors capable of sensing changes in the human breast, contacting a human breast with the breast shield and one or more sensors, applying a cyclical pressure to the breast, sensing changes in the breast by way of the one or more sensors, generating signals corresponding to the sensing of changes, and controlling the breastpump responsive to the generated signals.

Embodiments of this aspect of the present invention include the sensing of changes includes the sensing of changes in conductance. The sensing of changes may include the sensing of thermal changes, sensing of changes in acoustic properties, the sensing of changes in optical properties, the sensing of changes in conductance through a drop of impedance. The drop of impedance may be an amount from about 2 percent to about 20 percent, for instance. The drop of impedance may cause initiation of a change in breast pumping parameters of the microprocessor controlled breastpump. The drop in impedance may correspond to a let down reflex in the mother. The drop in impedance may be used to initiate a transition from a letdown sequence to an expression sequence of the microprocessor controlled breastpump.

Yet another aspect of the present invention is a system for sensing changes in a human breast, including a breast shield including a breast-receiving portion sized and shaped to receive a nipple and at least some surrounding breast. One or more sensors are connected to the breast-receiving portion and capable of sensing changes in the human breast. A device is adapted to receive output signals from the one or more sensors. Another embodiment of the system of the present invention includes a microprocessor controlled breastpump responsive to the device.

These and other aspects and advantages of the invention will be further understood upon consideration of the following drawings and related description, in which:

BRIEF DESCRIPTION OF THE DRAWINGS

FIG. 5 shows a perspective view of an alternate embodiment of a system for detecting changes in a human breast according to the present invention.

DETAILED DESCRIPTION OF A PRESENTLY PREFERRED EMBODIMENT

Figure 1:
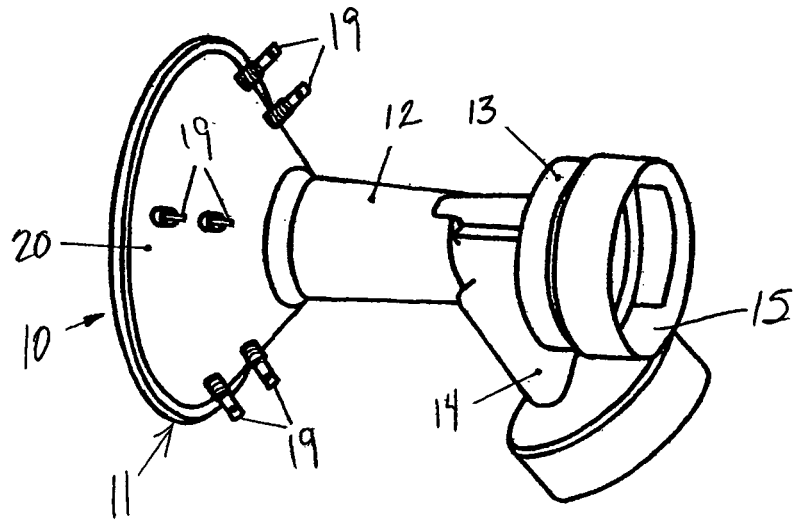
FIG. 1 shows a perspective diagrammatic view of one embodiment of a breast shield according to the invention.
Figure 2:
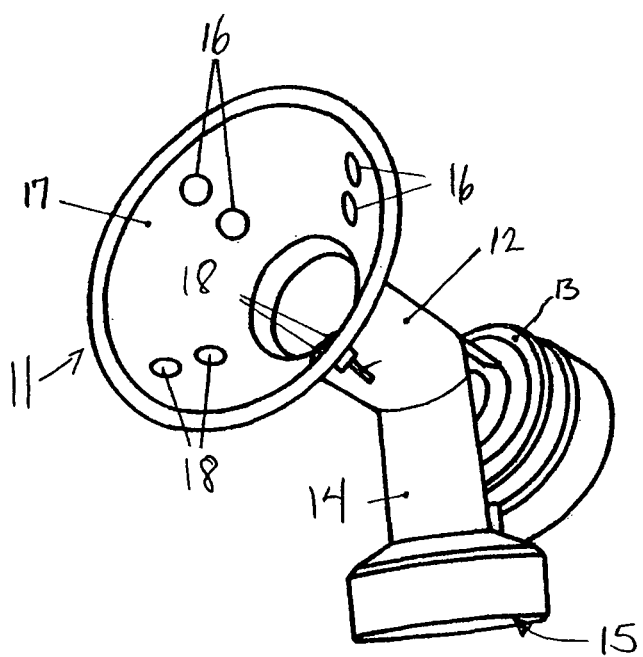
FIG. 2 shows a similar view looking at the open end of the breast shield of FIG. 1.

FIGS. 1 and 2 show a breast shield 10. The breast shield includes a portion having a truncated cone shape 11. The cone or funnel portion 11 is sized and shaped to be received on a breast and accept the nipple and at least some surrounding breast tissue. The funnel portion 11, via a cylindrical extension or tubular connection piece 12. The cylindrical extension 12 is sized and shaped to comfortably receive the nipple. The extension 12 leads to a first collar or attachment 13 for connecting to a breast pump (not shown) and a second collar or attachment 14 for connection to a milk-collecting container or bottle (not shown). In one preferred embodiment, each of the first and second attachment 13, 14 provides a conventional threaded engagement 15 with a breast pump or bottle as is known in the art. Other styles and shapes of breast shield 10 can be used to advantage.

The breast shield 10 with parts 11-14, which all may be made of transparent or translucent plastic for example, is itself largely of conventional design. The shield funnel 11 is provided with a number of sensing devices 16, as discussed in more detail herein, for example, electrodes, arranged at predetermined locations. The sensing devices are molded with, affixed through or otherwise attached to the shield funnel 11.

On the inside face 17 of the funnel 11 the electrodes include contact surfaces 18, positioned so as to contact the tissue of the breast when the breast shield is applied to the breast. The outside face 20 of the funnel wall includes connection contacts 19 for attaching the sensing devices 16 to an instrument (see FIG. 3) for monitoring the output of the sensing devices 16.

It will be noted the exemplary sensing devices depicted in FIGS. 1 and 2 have spaced pairs of metal electrodes, or the like, to function because one (or more) electrode is used to apply a voltage to the skin tissue of the breast and another electrode is spaced therefrom to detect current conveyed through the tissue. For example, during operation, a small voltage potential is applied between adjacent pairs of electrodes 16. The resistance between the adjacent pairs of electrodes 16 may be measured conventionally and the signal amplified, recorded, analyzed, or used as a signal or control input, to another device, such as a monitor or breastpump controller.

When the breast shield 10 is placed on a breast, the contact surfaces 18 may be integrated into and positioned flush within the inside surface 17 of the breast shield, while a desired voltage is applied via the connection contacts 19 (as parts of the electrodes leading through the funnel wall). The invention permits measurements via the electrodes 16 during the expression of breast milk. The corresponding device (see FIG. 3) for detecting, amplifying, measuring, recording and evaluating the signal can be integrated into a breast pump or can be a separate instrument.

It will be understood, depending on the type of information desired, instead of or in addition to the electrodes 16, other types of sensors can also be arranged in the breast shield, for example acoustic sensors, optical sensors or thermal sensors. It will be understood, that one with ordinary skill in the art will have sufficient knowledge of the types of sensors and associated instruments applicable to studying the function of human skin and tissue to use and adapt sensors and utilize the sensor output as desired.

Depending on the type of sensor 16, it does not necessarily need to have a contact surface 18. For example, in the case of optical sensors, it is sufficient for them to be disposed sufficiently close to the breast surface to detect changes in the breast. When using optical sensors, it is advisable of at least the area of the breast shield 10 immediately surrounding the sensor is made transparent to the optical wavelength used for the measurement, or at least no reflections are permitted on the inside face of the breast shield. Furthermore, depending on the type of sensors used, the breast shield 10 and its main body do not necessarily have to be made entirely of an electrically non-conducting material. If using electrodes as sensors, it may also suffice for only the areas of the breast shield 10 which are adjacent to the electrodes to be made electrically non-conducting, or otherwise electrically isolate the contact. As can be discerned from the Figures, the nipple of the mother's breast protrudes into the funnel opening 11 and into the cylindrical extension 12. The sensing devices 16 are thus preferably arranged at a distance from the nipple so that the latter is not disturbed during the expression of milk.

Figure 3:
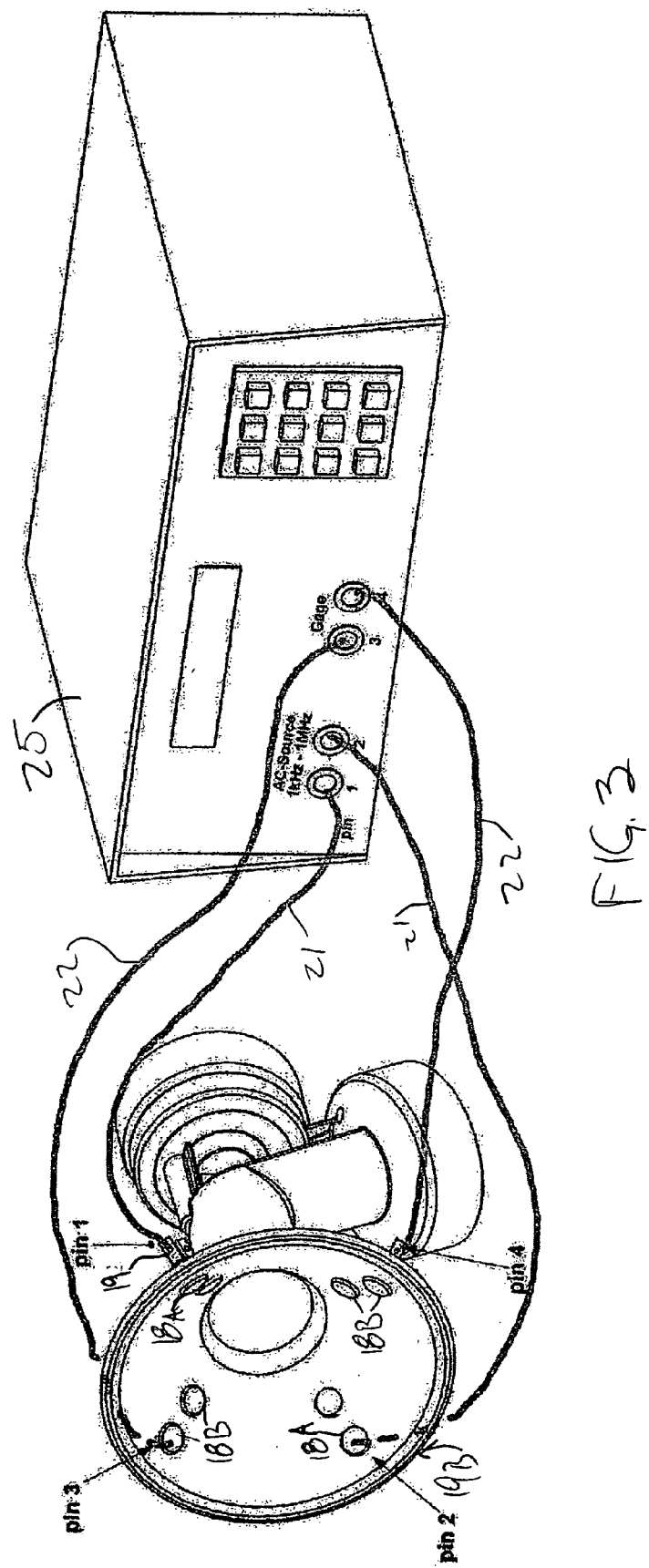
FIG. 3 shows a perspective view of a system for measuring changes in the human breast including a breast shield, sensors and monitoring instrumentation according to an embodiment of the present invention.

Turning to FIG. 3, the breast shield 10 of FIGS. 1 and 2 is shown attached to an instrument 25 for generating a supply voltage to a first pair of electrodes 18A, and receiving the current conducted to a second pair of electrodes 18B and performing an impedance measurement. In this embodiment, the first pair of electrodes 18A is attached to the instrument 25 with a first pair of wires 21 using pins 19 (see FIG. 1). The second pair of electrodes 18B is attached to the instrument 25 by way of a second pair of wires 22 to receive a signal in the form of an amount of current conducted through the subject tissue from the first pair of electrodes 18B. The resulting difference between the supply and sensed current conducted across and through the skin can be measured.

It has been found that conductance changes throughout the process of breast pumping. In particular, it has been found, in one example, that at the end of milk letdown (i.e., at the onset of milk expression) impedance measurements using the device of the present invention demonstrate a drop of about five to ten percent. This point roughly corresponds also to a rapid rise in milk production ("milk" mass) (See FIG. 4). Thus, a breast pump responsive to a detected change in conductance of the breast during milk pumping operating with an embodiment of the present invention can be programmed to be responsive to the change in signal. Advantageously, the breastpump can alter pumping parameters to adapt to the change in signal. For example, as disclosed in U.S. Pat. No. 6,547,756, it may be gleaned that the breast pump may adjust the amount of negative pressure applied to the breast and/or the cyclical frequency in response to a sensed change of impedance (see FIG. 1) corresponding to the end of the milk letdown phase.

Figure 4:
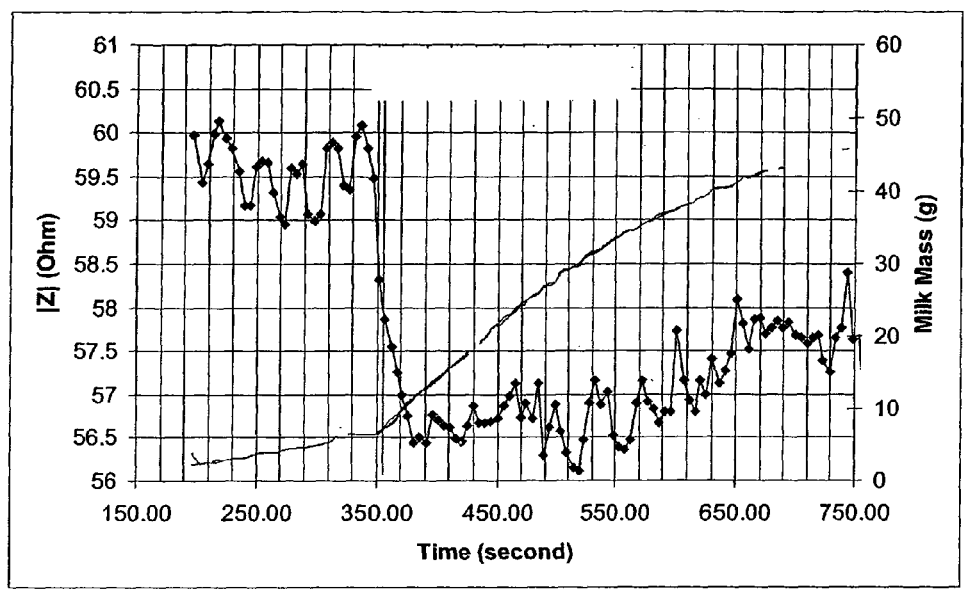
FIG. 4 shows a graph of conductance changes in the human breast while producing milk during breast pumping.

FIG. 4 shows a graph generated by the system of FIG. 3, wherein impedance drops appreciably at about the same time that the mother reports letdown. At the same point, the rate of milk production increases significantly. Conductance drops from about a value of 60 Ohms to a value of about 56.5 Ohms at letdown at about 350 seconds from the initiation of breast pumping.

Turning to FIG. 5, another embodiment of a system, using a breast shield 110 modified to incorporate optical sensing devices, is shown. This embodiment includes one or more sockets 150, formed in and through the wall of the funnel portion 120 of a breast shield, which are sized and shaped to receive a light guide, waveguide or similar light conveying device 130. A light source 125 is provided and connected to the light guide 130. Light is conveyed through the light guide 130 to the breast. Reflected light from the breast is received by and conveyed through the light guide 130 to an optical spectrum analyzing instrument 140. In this fashion, changes in the breast detectable by changes in the reflected light may be used in studying milk production and expression and may be used as a control signal in controlling a breastpump in a similar fashion as that described above.

While the apparatus and method herein disclosed forms a preferred embodiment of this invention, this invention is not limited to that specific apparatus and method, and changes can be made therein without departing from the scope of this invention, which is defined in the appended claims.

What is claimed is:

1. A device for detecting one or more parameters associated with breast tissue, including skin, during breastmilk expression in a human female, comprising:
   a breast shield having an interior part within which a portion of the breast is received including the nipple;
   a plurality of sensors associated with said breast shield, said plurality of sensors adapted to detect a parameter associated with breast tissue, including skin, during breastmilk expression;
   wherein said plurality of sensors are attached to said breast shield;
   wherein said plurality of sensors have a portion which extends to said breast shield interior part and is in contact with the breast; and
   wherein said plurality of sensors include an electrode extending from said contact through the breast shield and terminating in a connection for attachment to a wire.

2. The device of claim 1 wherein each said contact is electrically isolated.

3. The device of claim 2 wherein said plurality of sensors include a sensor which detects changes in an electrical field within the breast.

4. The device of claim 1 wherein said sensors include an optical sensor.

5. The device of claim 1 wherein said sensors include a sensor for detecting changes in a magnetic field within the breast.

6. The device of claim 1 wherein said sensors include a sensor for detecting pressure changes of the breast.

7. The device of claim 1 wherein said sensors include a sensor for detecting ultrasound.

* * * * *